US010255695B2

(12) United States Patent
Kowarschik et al.

(10) Patent No.: US 10,255,695 B2
(45) Date of Patent: Apr. 9, 2019

(54) CALCULATING A FOUR DIMENSIONAL DSA DATASET WITH VARIABLE SPATIAL RESOLUTION

(71) Applicant: SIEMENS HEALTHCARE GMBH, Erlangen (DE)

(72) Inventors: Markus Kowarschik, Nuremberg (DE); Sonja Gehrisch, Nuremberg (DE); Kevin Royalty, Fitchburg, WI (US); Sebastian Schafer, Madison, WI (US); Christopher Rohkohl, Brixen Im Thale (AT)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/854,105

(22) Filed: Dec. 26, 2017

(65) Prior Publication Data
US 2018/0182132 A1    Jun. 28, 2018

(30) Foreign Application Priority Data
Dec. 23, 2016  (DE) .......................... 10 2016 226 195

(51) Int. Cl.
*G06T 11/00* (2006.01)
*G06T 3/40* (2006.01)
(Continued)

(52) U.S. Cl.
CPC ............ *G06T 11/006* (2013.01); *A61B 6/504* (2013.01); *G06T 3/4007* (2013.01); *G06T 5/50* (2013.01);
(Continued)

(58) Field of Classification Search
CPC ....... G06T 11/006; G06T 3/4007; G06T 5/50; G06T 2207/10076; G06T 2207/20224;
(Continued)

(56) References Cited

U.S. PATENT DOCUMENTS 5,647,360 A  *  7/1997  Bani-Hashemi .......... G06T 5/50
                                                   382/130
8,643,642 B2 *  2/2014  Mistretta .............. A61B 6/4441
                                                   345/419
(Continued)

FOREIGN PATENT DOCUMENTS

CN          102622743 A        8/2012
CN          103177460 A        6/2013
(Continued)

OTHER PUBLICATIONS

Bescós, Javier Olivan, et al. "Volume measurement of intracranial aneurysms from 3D rotational angiography: improvement of accuracy by gradient edge detection." American journal of neuroradiology 26.10 (2005): 2569-2572.*
(Continued)

*Primary Examiner* — Michelle M Entezari
(74) *Attorney, Agent, or Firm* — Laurence Greenberg; Werner Stemer; Ralph Locher

(57) ABSTRACT

A method calculates a four-dimensional DSA dataset from x-ray datasets. Each of the x-ray datasets contains a two-dimensional x-ray projection of an examination volume in relation to a direction of projection and a recording time. A first three-dimensional DSA dataset of a first reconstruction volume is determined based on the x-ray datasets. The first reconstruction volume is a part of the examination volume. A second three-dimensional DSA dataset of a second reconstruction volume is determined based on the x-ray datasets. The second reconstruction volume is a part of the first reconstruction volume. The second three-dimensional DSA dataset is segmented. The x-ray datasets are normalized based on the first three-dimensional DSA dataset. A four-dimensional DSA dataset is calculated by back projection of the normalized x-ray datasets onto the segmented second three-dimensional DSA dataset. The four-dimensional DSA
(Continued)

dataset contains a number of third three-dimensional DSA datasets and associated time information.

14 Claims, 4 Drawing Sheets

(51) Int. Cl.
  *G06T 5/50* (2006.01)
  *A61B 6/00* (2006.01)
(52) U.S. Cl.
  CPC .............. *G06T 2207/10076* (2013.01); *G06T 2207/20224* (2013.01); *G06T 2207/30101* (2013.01); *G06T 2211/404* (2013.01)
(58) Field of Classification Search
  CPC ..... G06T 2207/30101; G06T 2211/404; A61B 6/504
  See application file for complete search history.

(56) References Cited

U.S. PATENT DOCUMENTS

| | | | |
|---|---|---|---|
| 8,654,119 B2* | 2/2014 | Mistretta | A61B 6/02 345/419 |
| 8,963,919 B2* | 2/2015 | Mistretta | A61B 6/032 345/424 |
| 9,414,799 B2* | 8/2016 | Mistretta | A61B 6/032 |
| 9,508,157 B2* | 11/2016 | Schafer | G06T 11/005 |
| 9,786,069 B2* | 10/2017 | Schafer | G06T 11/006 |
| 2011/0038517 A1* | 2/2011 | Mistretta | A61B 6/02 382/128 |
| 2012/0041318 A1* | 2/2012 | Taylor | A61B 5/02007 600/504 |
| 2012/0114217 A1 | 5/2012 | Mistretta et al. | |
| 2012/0170820 A1 | 7/2012 | Declerck et al. | |
| 2013/0121555 A1 | 5/2013 | Bruder et al. | |
| 2014/0142423 A1* | 5/2014 | Mistretta | A61B 6/4441 600/424 |
| 2014/0376791 A1 | 12/2014 | Heigl et al. | |
| 2015/0201897 A1* | 7/2015 | Kyriakou | A61B 5/489 600/419 |
| 2015/0257724 A1* | 9/2015 | Lautenschlager | A61B 6/504 600/431 |
| 2016/0048959 A1* | 2/2016 | Kowarschik | G06T 7/0012 600/425 |
| 2016/0267704 A1* | 9/2016 | Mistretta | A61B 6/4441 |
| 2017/0256077 A1* | 9/2017 | Schafer | G06T 11/006 |

FOREIGN PATENT DOCUMENTS

| | | |
|---|---|---|
| CN | 104783825 A | 7/2015 |
| DE | 102014201134 A1 | 7/2015 |

OTHER PUBLICATIONS

Copeland, Andrew D., et al. "Spatio-temporal data fusion for 3D+T image reconstruction in cerebral angiography." IEEE Transactions on Medical Imaging 29.6 (2010): 1238-1251. APA.*

Felkel, Petr, Rainer Wegenkittl, and Armin Kanitsar. "Vessel tracking in peripheral CTA datasets-an overview." Computer Graphics, Spring Conference on, 2001.. IEEE, 2001.APA.*

Sedlacik, Jan, Andreas Frölich, Johanna Spallek, Nils D. Forked, Tobias D. Faizy, Franziska Werner, Tobias Knopp, Dieter Krause, Jens Fiehler, and Jan-Hendrik Buhk. "Magnetic particle imaging for high temporal resolution assessment of aneurysm hemodynamics." PloS one 11, No. 8 (2016): e0160097. (Year: 2016).*

Badea CT, Hedlund LW, DE Lin M, Boslego JF, Johnson GA. Functional imaging in small animals using tomographic digital subtraction angiography. InBiomedical Imaging: Nano to Macro, 2006. 3rd IEEE International Symposium on Apr. 6, 2006 (pp. 1208-1211). IEEE. (Year: 2006).*

Brian J. Davis, et al.; "Volumetric limiting spatial resolution analysis of four-dimensional digital subtraction angiography"; Journal of Medical Imaging; 2016; pp. 013503-1-013503-9; vol. 3; No. 1.

B. Davis, et al.; "4D Digital Subtraction Angiography: Implementation and Demonstration of Feasibility"; American Society of Neuroradiology; 2013; pp. 1-8; vol. 34; http://dx.doi.org/10.3174/ajnr.A3529.

Royalty, Kevin: "4D DSA: New Methods and Applications for 3D Time-Resolved Angiography for C-arm CT Interventional Imaging", Dec. 31, 2014 (Dec. 31, 2014), XP055369893, Ann Arbor, United States ISBN: 978-1-321-16653-8, found on the Internet May 5, 2017: URL: http://search.proquest.com/docview/1615085787/abstract/A462590FFB214500PQ/1.

* cited by examiner

CALCULATING A FOUR DIMENSIONAL DSA DATASET WITH VARIABLE SPATIAL RESOLUTION

CROSS-REFERENCE TO RELATED APPLICATION

This application claims the benefit, under 35 U.S.C. § 119, of German patent application DE 10 2016 226 195.9, filed Dec. 23, 2016; the prior application is herewith incorporated by reference in its entirety.

BACKGROUND OF THE INVENTION

Field of the Invention

In digital subtraction angiography (abbreviated to DSA) one or more vessels are shown by x-ray recordings. To suppress further structures in the examination volume, images of a vessel on its own are combined with images of the vessel including a contrast medium that is to be found in the vessel. The contrast medium is introduced into the vessel here during the examination in order to determine parameters, in particular hydrodynamic parameters of a fluid, wherein the fluid flows in the vessel.

In four-dimensional DSA a time-resolved series of three-dimensional DSA image data is provided by an image reconstruction method. Normalized two-dimensional x-ray projections of an examination volume are back projected here together with time information into a volume element. The two-dimensional x-ray projections usually originate here from a rotating recording protocol of a C-arm x-ray arc.

The multiplicative back projection is subject to restrictions if a number of vessels or a number of vessel sections overlap in the two-dimensional x-ray projections. In this case it is not evident from a single x-ray projection as to the overlapping vessel to which an x-ray signal, in particular an intensity value or an x-ray absorption coefficient, must be assigned. This is the case in particular when overlaps occur with vessels outside the reconstruction volume.

The number of voxels in a three-dimensional image dataset is defined on the basis of standards in medical imaging such as for example digital imaging and communications in medicine (DICOM), e.g. as 256×256×256 or as 512×512×512.

It is known that multiplicative back projection can be carried out for a maximum size of reconstruction volume, in order to resolve a possible overlap of vessels in the best possible way. Because of the number of voxels defined by standards however, the spatial resolution is thus limited by the size of the reconstruction volume.

It is further known that multiplicative back projection can be carried out for a smaller reconstruction volume. Although the resolution is improved here, vessels or vessel sections outside the reconstruction volume can falsify the results.

SUMMARY OF THE INVENTION

It is therefore the object of the present invention, taking into account vessels outside the reconstruction volume, to achieve a variable, in particular a finer spatial resolution of the reconstruction volume.

The inventive manner in which the object is achieved will be described below in relation to the claimed devices and also in relation to the claimed method. Features, advantages or alternate forms of embodiment mentioned here are likewise also to be transferred to the other claimed subject matter and vice versa. In other words the physical claims (which are directed to a device for example) can also be further developed with features that are described or claimed in conjunction with a method. The corresponding functional features of the method are embodied in such cases by corresponding physical modules.

The invention is based on x-ray datasets relating to an examination volume being received by means of an interface, wherein each of the x-ray datasets contains a two-dimensional x-ray projection of the examination volume relating to a direction of projection and a recording time of the x-ray projection. Here the examination volume contains at least one vessel, wherein the vessel can contain a contrast medium, and wherein the spatial density of the contrast medium can change over time. The recording time corresponds to the point in time of the recording of the two-dimensional x-ray projection. A two-dimensional x-ray projection is in particular spatially two-dimensional. The x-ray projections can in particular also involve DSA x-ray projections.

The invention is further based on a first three-dimensional DSA dataset of a first reconstruction volume on the basis of the x-ray datasets being determined by a calculation unit, wherein the first reconstruction volume is a part of the examination volume or is identical to the latter. A three-dimensional dataset is in particular spatially three-dimensional.

The invention is further based on a second three-dimensional DSA dataset of a second reconstruction volume on the basis of the x-ray datasets being determined by the calculation unit, wherein the second reconstruction volume is a part of the first reconstruction volume. Here the determining of the second three-dimensional DSA dataset is in particular only based on the x-ray datasets, i.e. in particular not on the first three-dimensional DSA dataset.

The invention is further based on the second three-dimensional DSA dataset being segmented by the calculation unit. Here the DSA dataset is segmented into at least two parts, wherein a first part contains at least one vessel contained in the second reconstruction volume and the inside of the vessel, and a second part comprises the other components of the second reconstruction volume. The first part can also comprise a number of vessels contained in the reconstruction volume and the inside of the vessels.

The invention is further based on the x-ray datasets being normalized by the calculation unit on the basis of the first three-dimensional DSA dataset.

The invention is further based on a four-dimensional DSA dataset being calculated by back projection of the normalized x-ray datasets onto the segmented second three-dimensional DSA dataset by the calculation unit, wherein the four-dimensional DSA dataset contains a number of third three-dimensional DSA datasets as well as associated time information. Here each of the third three-dimensional DSA datasets is assigned time information. Here the time information belonging to a third three-dimensional DSA dataset corresponds in particular to the time at which the state of the vessel shown corresponds to the mapping in the three-dimensional DSA dataset. In particular each of the voxels of each of the third three-dimensional DSA datasets contains time information. Time information can in particular also be a time coordinate. A back projection can in particular be a multiplicative back projection.

The inventors have recognized that by the first determination of a first three-dimensional DSA dataset and by the second determination of a second three-dimensional DSA dataset, the normalization can be based on the first three-dimensional DSA dataset and the segmentation and also the calculation of the four-dimensional DSA dataset can be based on the second three-dimensional DSA dataset. Since the first reconstruction volume is larger than the second reconstruction volume, a variable, in particular a better, spatial resolution of the second three-dimensional DSA datasets and simultaneously information about further vessels mapped in the x-ray projections from the larger first reconstruction volume can be used.

According to a further aspect of the invention, each third three-dimensional DSA dataset of the four-dimensional DSA dataset is calculated by back projection from precisely one of the two-dimensional x-ray datasets, wherein the associated time information corresponds to the recording time of the two-dimensional x-ray dataset. The inventors have recognized that, through the unique assignment of an x-ray projection to a three-dimensional DSA dataset, the time information belonging to the three-dimensional DSA dataset can be determined uniquely and thereby without errors.

According to a further aspect of the invention, the method further contains a third determination of a confidence value for at least one first pixel of at least one of the x-ray projections on the basis of the first three-dimensional DSA dataset, an assignment of the confidence value to a first voxel of at least one of the third three-dimensional DSA datasets, wherein the value of the first voxel is based on the value of the first pixel, as well as an interpolation of the four-dimensional DSA dataset on the basis of the confidence value. The value of the first voxel is based in particular on the value of the first pixel, when the value of the first voxel is calculated by back projection from the value of the first pixel. The third determination, the assignment and the interpolation are each carried out here by means of the calculation unit. The inventors have recognized that it is possible by an interpolation to establish valid and less fault-susceptible four-dimensional DSA datasets even with vessels or vessel parts of which the x-ray projections overlap in relation to one or more directions of projection at one or more points in time.

According to a further possible aspect of the invention, an interpolated intensity value of a voxel of a first of the third three-dimensional DSA datasets is only based on the intensity values of the corresponding voxels in the third three-dimensional DSA datasets. In this case a corresponding voxel is in particular a spatially corresponding voxel. The inventors have recognized that the gradient of the concentration of a contrast medium in relation to the time is smaller and more even than it is in relation to one of three spatial directions, and that therefore a temporal interpolation produces especially good results. In particular the interpolated intensity value of the first voxel is based only on the intensity values of one of the second voxels corresponding to the first voxel in a second of the third three-dimensional DSA datasets and of a third voxel corresponding to a first voxel in a third of the third three-dimensional DSA dataset. In particular the interpolated intensity value is determined by a linear interpolation. The inventors have recognized that a linear interpolation is able to be carried out especially easily and robustly in relation to an overmatching.

According to a further aspect of the invention, the confidence value of the first pixel of an x-ray projection falls monotonously with a number of the vessel sections projected onto the first pixel in the first three-dimensional DSA dataset, wherein the vessel sections are projected in the direction of projection of the x-ray projection. The inventors have recognized that the reliability of back-projected three-dimensional decreases with the number of vessel sections overlapping in an x-ray projection, and therefore the number of the overlapping vessel sections is a suitable criterion for the reliability or exactness of a pixel value.

According to a further aspect of the invention, the interpolation relates to voxels to which a confidence value smaller than a threshold value is assigned. The inventors have recognized that voxels for which, because of overlapping, no secure information about the intensity value is possible, can be selected especially quickly and easily on the basis of the threshold value. The threshold value can be selected in particular so that all voxels are interpolated with a confidence value smaller than the maximum allocated confidence value. Through this the intensity values of all voxels that cannot be determined solely by the associated x-ray projection and therefore exhibit an uncertainty or incorrect data, can be improved or corrected by interpolation.

According to a further aspect of the invention, the first and the second three-dimensional DSA dataset each contain homogeneous voxels. The voxels of a DSA dataset are in particular homogeneous when all pairs of two voxels from the DSA dataset each have the same spatial extent in relation to a first axis parallel to a first voxel edge, in relation to a second axis parallel to a second voxel edge and orthogonal to the first axis and in relation to a third axis parallel to a third voxel edge and orthogonal to the first axis and to the second axis. The voxels of a DSA dataset can in particular also be isotropic, meaning that each voxel of a DSA dataset has the same extent in relation to the first axis, the second axis and the third axis. The value of a voxel can in particular be an x-ray absorption coefficient or a binary value, wherein the binary value designates whether a voxel belongs to a particular structure. The inventors have recognized that the method can be carried out especially quickly and efficiently with homogeneous voxels, since the back projection does not have to be matched to the geometry of individual voxels and can therefore be calculated vectorized and in parallel.

According to a further aspect of the invention, the orientation of the voxels in the first three-dimensional DSA dataset corresponds to the orientation of the voxels in the second three-dimensional DSA dataset. The orientation of a first voxel in the first three-dimensional DSA dataset corresponds in particular to the orientation of a second voxel in the second three-dimensional DSA dataset, if each edge of the first voxel is parallel to an edge of the second voxel. The inventors have recognized that calculation simplifications, which allow an especially fast and simple execution of the method, are produced in the method by the same orientation of the voxels.

According to a further aspect of the invention, the length of the edges of the voxels of the second three-dimensional DSA dataset parallel in relation to a first coordinate axis is smaller than the length of the edges of the voxels of the first three-dimensional DSA dataset parallel in relation to the first coordinate axis. In particular the length of the edges of the voxels of the second three-dimensional DSA dataset parallel to a second or third coordinate axis can be smaller than the length of the edges of the voxel of the first three-dimensional DSA dataset parallel to a second or third coordinate axis. The inventors have recognized that the spatial resolution of the resulting four-dimensional DSA dataset can be improved by such a ratio of the edge lengths.

According to a further aspect of the invention the number of the voxels in the first three-dimensional DSA dataset is equal to the number of the voxels in the second three-dimensional DSA dataset. The inventors have recognized that by having the same number of voxels in the first and in the second three-dimensional DSA dataset, both DSA datasets can be stored in a similar data structure, in particular in a DICOM dataset. This simplifies memory and data management and makes possible a standardized data exchange.

According to a further aspect of the invention, the edge lengths of the voxels of the second three-dimensional DSA dataset are larger than the edge length of the pixels of the x-ray dataset. The inventors have recognized that, by such a ratio of the edge lengths, a pixel of one of the x-ray projections of the x-ray datasets is at most assigned to a voxel of the second three-dimensional DSA dataset. Through this the value of a voxel is always determined precisely by the value of at least one pixel and does not have to be determined by an interpolation.

The invention further relates to a DSA calculation unit for calculating a four-dimensional DSA dataset. The DSA calculation unit contains an interface and a calculation unit. The interface is embodied for receiving x-ray datasets relating to an examination volume. Each of the x-ray datasets includes a two-dimensional x-ray projection of the examination volume in relation to a direction of projection and a recording time of the x-ray projection. The calculation unit is embodied for a first determination of a first three-dimensional DSA dataset of a first reconstruction volume on the basis of the x-ray datasets. The first reconstruction volume is a part of the examination volume or is identical to the volume. The calculation unit is furthermore embodied for a second determination of a second three-dimensional DSA dataset of a second reconstruction volume on the basis of the x-ray datasets. The second reconstruction volume is a part of the first reconstruction volume. The calculation unit is still furthermore embodied for the segmentation of the second three-dimensional DSA dataset and for normalization of the x-ray datasets on the basis of the first three-dimensional DSA dataset. The calculation unit is embodied for calculation of a four-dimensional DSA dataset by back projection of the normalized x-ray datasets to the segmented second three-dimensional DSA dataset. The four-dimensional DSA dataset contains a number of third three-dimensional DSA datasets as well as associated time information.

Such a DSA calculation unit can be embodied in particular to carry out the previously described inventive method and its aspects. The DSA calculation unit is embodied to carry out this method and its aspects in that the interface and the calculation unit are embodied to carry out the corresponding method steps. The invention further relates to an x-ray unit, embodied for recording of x-ray datasets and also comprising an inventive DSA calculation unit.

The invention also relates to a computer program product with a computer program as well as a computer-readable medium. A largely software-based realization has the advantage that DSA calculation units already used previously can be upgraded in a simple manner in order to operate in the inventive method. Such a computer program product, as well as the computer program, can possibly comprise additional elements such as e.g. documentation and/or additional components and can also have hardware components, such as e.g. hardware keys (dongles etc.) for use of the software.

An x-ray projection is a two-dimensional projection of an examination volume by means of x-rays in a direction of projection, which in particular can comprise a number of pixels. In this case each pixel is allocated an x-ray intensity value, which is a measure for the x-ray intensity encountered in this pixel. The incident x-ray intensity depends on the number, the size, the shape and the material of the objects to be found in the examination volume. An edge length of an edge of a pixel is the length in the examination volume, which corresponds to the edge of the pixel.

A DSA x-ray projection of an examination volume can be determined from a first x-ray projection and a second x-ray projection of the examination volume, wherein the first x-ray projection and the second x-ray projection have been recorded in relation to the same direction of projection, and wherein, at the time of the recording of the first x-ray projection, a contrast medium distribution other than that present at the time of the recording of the second x-ray projection has been present in the examination volume. The DSA x-ray projection can then be computed from the difference between the x-ray intensities of the first x-ray projection and the second x-ray projection.

A three-dimensional dataset of the examination volume can be reconstructed from a number of x-ray projections from different directions of projection. If the number of x-ray projections involves DSA x-ray projections, a three-dimensional DSA dataset of the examination volume can be reconstructed. A three-dimensional dataset or a three-dimensional DSA dataset can in particular comprise a number of voxels, to which an x-ray absorption or an x-ray intensity is assigned. The x-ray absorption can be measured in Hounsfield units (abbreviated to HU).

A four-dimensional DSA dataset contains a number of three-dimensional voxels, to which time information is assigned. In an equivalent manner a four-dimensional DSA dataset can also be described by it containing a number of three-dimensional DSA datasets, wherein a three-dimensional DSA dataset is assigned time information. Time information can be acquired as time coordinates, and the four-dimensional DSA dataset can be acquired as a time sequence or film of three-dimensional DSA datasets.

A back projection is a method that establishes, from one or more two-dimensional projections of a three-dimensional examination volume, data relating to the three-dimensional examination volume. The data relating to the three-dimensional examination volume can in particular involve absorption coefficients or Hounsfield Units. Since a two-dimensional projection contains less information than the three-dimensional examination volume, further information can be used for a back projection, for example a segmentation of the examination volume or of a reconstruction volume.

Other features which are considered as characteristic for the invention are set forth in the appended claims.

Although the invention is illustrated and described herein as embodied in a calculating a four-dimensional DSA dataset with variable spatial resolution, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
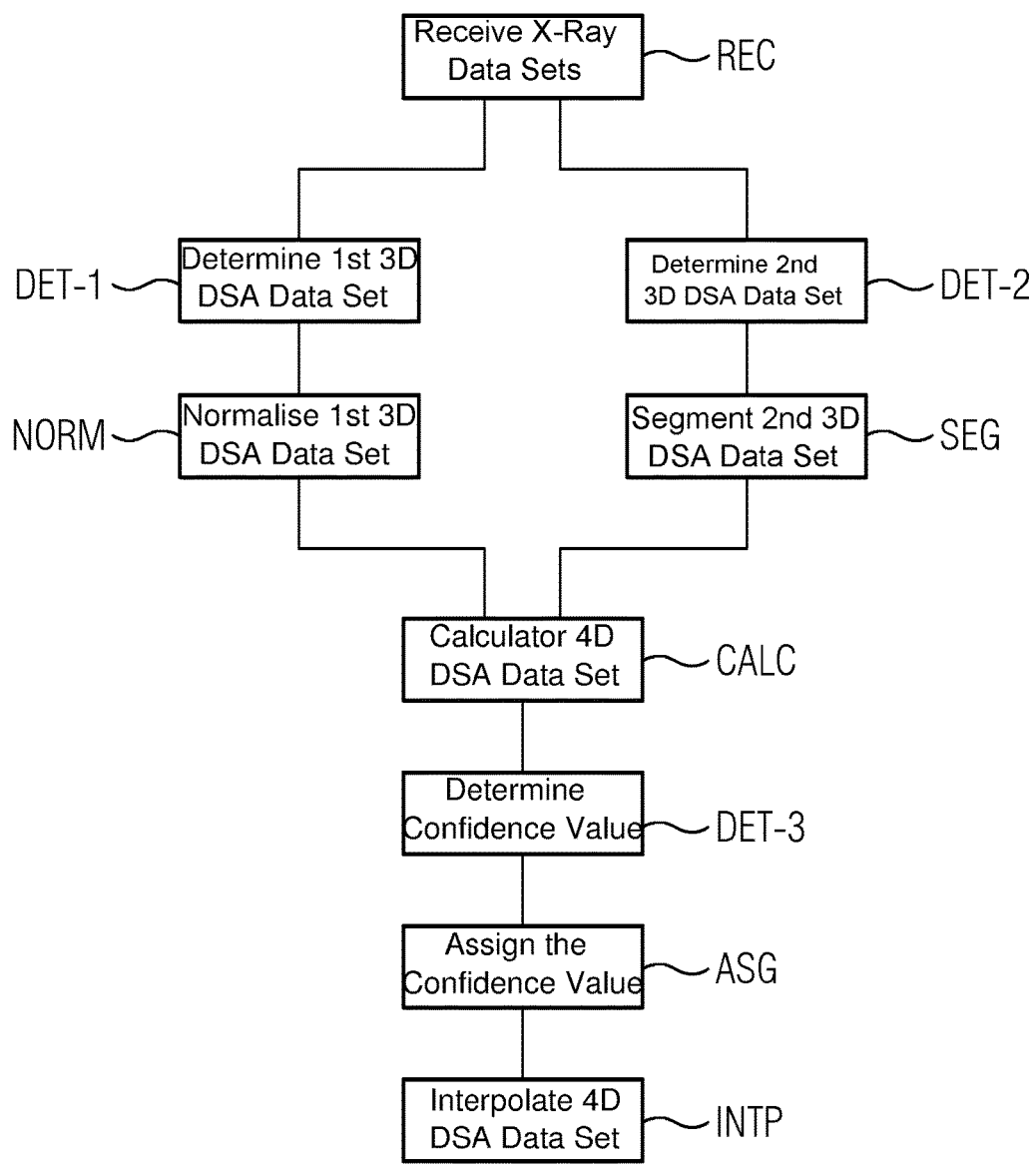
FIG. 1 is a flow diagram of a method for calculating a four-dimensional DSA dataset from x-ray datasets according to the invention.

The first step of an exemplary embodiment of the method shown is the receipt REC of x-ray datasets 500 relating to an examination volume 400 by means of an interface 201. Each of the x-ray datasets 500 contains a two-dimensional x-ray projection 501.1, . . . , 501.4 of the examination volume 400 in relation to a direction of projection and a recording time of the x-ray projection 501.1, . . . , 501.4.

In the exemplary embodiment shown the x-ray projections 501.1, . . . , 501.4 have been recorded with a C-arm x-ray device 300. Precisely two x-ray datasets 500 are recorded here for each direction of projection, wherein no x-ray contrast medium is present in the first vessel 403 in the first x-ray dataset from each direction of projection in each case, and wherein x-ray contrast medium is present in the first vessel 403 in the second x-ray dataset in each case. In this case the x-ray datasets are recorded without x-ray contrast medium such that the C arm 303 rotates at a predetermined angle around the examination volume 400 and x-ray projections are recorded at a constant time interval. Furthermore the x-ray datasets 500 with x-ray contrast medium are recorded such that the C arm 303 rotates around the examination volume 400 at the predetermined angle and during this process x-ray projections 501.1, . . . , 501.4 are recorded at the same constant interval.

For each series of recordings the C arm 303 of the C-arm x-ray device 300 rotates by 260° in 12 seconds and in doing so records 304 x-ray projections from different directions of projection. Recording parameters containing other angles of rotation, rotation times and numbers of projections are also possible, in particular recording parameters such as lead to x-ray datasets that are suitable for a three-dimensional reconstruction. Angles of rotation that are greater than the sum of 180° and the opening angle of the x-rays of the x-ray source 301 are particularly suitable here, in particular angles of rotation of greater than 200°. In the recording of the x-ray projections 501.1, . . . , 501.4 with contrast medium the C arm 303 can rotate in the same circumferential direction as for the recording of the x-ray projections without contrast medium. In this case the C arm 303 must return to its starting position between the recordings. The C arm 303 can however also rotate in the circumferential direction opposite to that for the recording of the x-ray projections without contrast medium.

A two-dimensional DSA x-ray projection can then be established from a first x-ray dataset without contrast medium and a second x-ray dataset with contrast medium in each case, wherein the x-ray projections of the first and of the second x-ray dataset have been recorded from the same direction of projection, by subtraction of the intensity values of the x-ray projection of the second x-ray dataset from the x-ray projection of the first x-ray dataset.

As an alternative however it is also possible in this step of the method for x-ray datasets 400 containing DSA x-ray projections to be received directly.

Further steps of the exemplary embodiment of the method shown are the first determination DET-1 of a first three-dimensional DSA dataset of a first reconstruction volume 401 on the basis of the x-ray dataset 500 by means of a calculation apparatus 202. The first reconstruction volume 401 is a part of the examination volume 400 or is identical to said volume. A second determination DET-2 of a second three-dimensional DSA dataset of a second reconstruction volume 402 on the basis of the x-ray dataset 500 by means of the calculation apparatus 202 is performed. The second reconstruction volume 402 is part of the first reconstruction volume 401. The second three-dimensional DSA dataset is in particular not based on the first three-dimensional DSA dataset. Furthermore the order in which the first determination DET-1 and the second determination DET-2 are carried out is not relevant.

In the exemplary embodiment shown, the first determination DET-1 and the second determination DET-2 are each based on the two-dimensional DSA x-ray projections established from a subtraction. The first determination DET-1 and the second determination DET-2 can in particular only be based on those two-dimensional DSA-x-ray projections in which the first vessel 403 to be examined is filled completely or to a large extent with contrast medium.

In the exemplary embodiment shown, the first three-dimensional DSA dataset and the second three-dimensional DSA dataset are determined by means of a cone beam reconstruction from the two-dimensional x-ray projections or the two-dimensional DSA x-ray projections. However other reconstruction methods are also possible, for example a fan beam reconstruction. The Hounsfield Units of the respective reconstruction volume are determined here.

In the exemplary embodiment shown, the first reconstruction volume 401 is identical to the examination volume 400. The first reconstruction volume 401 can however also be smaller than the examination volume 400 and be contained in the examination volume 400. The second reconstruction volume 402 is smaller than the first reconstruction volume 401 and is part of the first reconstruction volume 401. In the exemplary embodiment shown the first reconstruction volume 401 and the second reconstruction volume 402 are embodied in the shape of a cube. However other geometries, in particular a rectangular geometry, are conceivable for the reconstruction volumes 401, 402.

In the exemplary embodiment shown, both the first three-dimensional DSA dataset and also the second three-dimensional DSA dataset consist of the same number of isotropic voxels, and indeed of 512×512×512 voxels, which corresponds to the DICOM standard. However other numbers of voxels are possible, in particular also differing numbers of voxels are possible, in particular also 256×256×256 voxels, which likewise corresponds to a DICOM standard. Furthermore non-isotropic voxels are possible. Through the same number of voxels and the different reconstruction volume 401, 402, the second three-dimensional DSA dataset has a better spatial resolution than the first three-dimensional DSA dataset. Furthermore the voxels of the first three-dimensional DSA dataset have the same alignment as the voxels of the second three-dimensional DSA dataset. They can however also have other alignments.

A further step of the exemplary embodiment of the method shown is the segmentation SEG of the second DSA dataset by means of the calculation apparatus 202. In the exemplary embodiment shown the segmentation SEG is by means of a threshold value segmentation, thus all voxels of the second DSA dataset are assigned with Hounsfield Units via the threshold value of a first region, which corresponds here to a first vessel 403, furthermore all voxels of the second DSA dataset are assigned with Hounsfield Units below the threshold value of a second region. However other methods are possible for segmentation, for example region growing or active shape models. The result of the segmentation can be expressed as function $C_2$, wherein the function $C_2$ assigns a voxel with spatial three-dimensional coordinate x to a value $C_2(x)$ if the voxel lies in the first region, wherein the value $C_2(x)$ corresponds to the value of the voxel in the second DSA dataset, and wherein the function $C_2$ assigns a voxel with the spatial three-dimensional coordinate x to a value $C_2(x)=0$ if the voxel lies in the second region.

A further step of the exemplary embodiment of the method shown is the normalization NORM of the x-ray datasets 500 on the basis of the first three-dimensional DSA dataset by means of the calculation apparatus 202, wherein the normalization in this exemplary embodiment is given by the following functional relationship:

$$p_N(t, u) = \frac{p(t, u)}{\int_{L(t,u)} I_1(l) dl}$$

Here u is a two-dimensional spatial coordinate in the coordinate system of the x-ray detector 302, and t is a temporal coordinate, thus in particular time information. Furthermore $I_1(I)$ designates the intensity value of the first three-dimensional DSA dataset at a three-dimensional spatial coordinate I. The one-dimensional path L(t,u) corresponds to the straight line through the point-type x-ray sources 301 and the point u on the x-ray detector 302 at the recording time t. The path L(t,u) is furthermore dependent on the temporal coordinate t, because the spatial position of the x-ray source 301 and of the x-ray detector 302 change with the temporal coordinates t. The size p(t,u) describes the intensity value of the x-ray projection recorded at the recording time t in the detector coordinate u. The result $p_N(t,u)$ is the normalized intensity value of the x-ray projection recorded at the time t in the detector coordinate u.

A further step of the exemplary embodiment of the method shown is the calculation CALC of a four-dimensional DSA dataset by back projection of the normalized x-ray datasets 500 to the segmented second three-dimensional DSA dataset by the calculation apparatus 202, wherein the four-dimensional DSA dataset contains a number of third three-dimensional DSA datasets as well as associated time information. In this exemplary embodiment a multiplicative back projection is used, which is given by the following functional relationship:

$$f(t, x) = C_2(x) \frac{p_N(t, A(t, x))}{K * \int_{L(t,A(t,x))} I_2(l) dl}$$

Here x is a three-dimensional spatial coordinate and t is a temporal coordinate, thus in particular time information. The tuple (t,x) can therefore be expressed as a four-dimensional coordinate. Furthermore $I_2(x)$ designates the second three-dimensional DSA dataset. A(t,x) designates the projection of the spatial coordinate x at recording time t to the spatial two-dimensional detector coordinate u=A(t,x). Furthermore K designates an optional convolution kernel, the operator * designates a convolution and $C_2(x)$ designates the function belonging to the segmentation of the second three-dimensional DSA dataset. Furthermore f(t,x) designates the four-dimensional DSA dataset, which contains a number of third three-dimensional DSA datasets x), $f(t_N, x)$.

A further optional step of the exemplary embodiment of the method shown is a third determination DET-3 of a confidence value for at least one first pixel of at least one of the x-ray projections 501.1, 501.2, 501.3, 501.4 on the basis of the first three-dimensional DSA dataset. In the exemplary embodiment shown the confidence value of a pixel of one of the x-ray projections 501.1, 501.2, 501.3, 501.4 is a measure for the number of the vessels 403, 404 and/or vessel sections 403.1, 403.2, which are mapped onto the pixel. The confidence value here is 1, if only precisely one vessel 403, 404 and/or vessel section 403.1, 403.2 is mapped onto the pixel, otherwise the confidence value falls with the number of vessels 403, 404 and/or vessel sections 403.1, 403.2 mapped onto the pixel.

The confidence value of a first pixel is determined by the one-dimensional x-ray intensity distribution along a beam starting from the x-ray source 301 to the first pixel is established from the first three-dimensional DSA dataset. The number of vessels 403, 404 and/or vessel sections 403.1, 403.2 projected onto the first pixel is then the number of the vessels 403, 404 and/or vessel sections 403.1, 403.2 through which this beam(s) passes. The number of traversed vessels 403, 404 and/or vessel sections 403.1, 403.2 can be established on the basis of the gradients of the x-ray intensity distribution, which shows edges of vessels 403, 404 and/or vessel sections 403.1, 403.2. The establishment of the number of traversed vessels 403, 404 and/or vessel sections 403.1, 403.2 can further include empirical values for the average size of a vessel 403, 404 and/or vessel section 403.1, 403.2. As an alternative it is also possible to segment the first three-dimensional DSA dataset and to determine the number of traversed vessels 403, 404 and/or vessel sections 403.1, 403.2 on the basis of the segmentation. As an alternative it is likewise possible to determine a confidence value on the basis of the number of voxels of the first three-dimensional DSA dataset through which the beam passes, wherein the voxels have a value above a threshold value.

A further optional step of the exemplary embodiment of the method shown is an assignment ASG of the confidence value to a first voxel of at least one of the third three-dimensional DSA datasets, wherein the value of the first voxel is based on the value of the first pixel, wherein the first voxel is assigned to the first pixel via the back projection. The value of the first voxel of one of the third three-dimensional DSA datasets is based in this case on the value of the first pixel, if the recording time of the x-ray projection comprising the first pixel and the time information of the three-dimensional DSA dataset belonging to the third three-dimensional DSA dataset belonging to the first voxel correspond to one another, and when the beam from the x-ray source 301 to the first pixel at the recording time passes through the first voxel. In the exemplary embodiment shown the confidence value of each pixel of each of the x-ray projections is assigned to the corresponding voxels of the third three-dimensional DSA datasets. It is however also possible to undertake the assignment only for a limited number of pixels from x-ray projections 501.1, . . . , 501.4 or of voxels of the third three-dimensional DSA datasets.

A further optional step of the exemplary embodiment of the method shown is an interpolation INTP of the four-dimensional DSA dataset on the basis of the confidence value. In this case the four-dimensional DSA dataset is interpolated in the exemplary embodiment shown such that intensity values of those voxels of those third three-dimensional DSA datasets to which a confidence value smaller than a threshold value is assigned is interpolated. In this exemplary embodiment the maximum confidence value is selected as the threshold value, so that there is interpolation for those voxels to which, because of overlays of vessels 403, 404 and/or vessel sections 403.1, 403.2, no exact intensity value can be allocated. In the exemplary embodiment shown, the interpolation for a first voxel in one of the third three-dimensional DSA datasets is only done with reference to the intensity values of the spatial corresponding voxels of the other of the third three-dimensional DSA datasets, thus in particular only a temporal interpolation. In this case two voxels correspond to one another in particular spatially if their position is described by the same spatial coordinates. It is however also possible to use the intensity values of other voxels on their own or additionally, and thereby to carry out a spatial interpolation on its own or in addition. Furthermore, in the exemplary embodiment shown there is a temporal linear interpolation between the intensity value of a spatially corresponding second voxel and a spatially corresponding third voxel as checkpoints, wherein the maximum confidence value is assigned to the second voxel and the third voxel. Here the time information assigned to the second voxel is smaller than the first time information assigned to the first voxel. Furthermore there is no other spatially corresponding voxel with a maximum confidence value, to which time information between the second time information and the first time information is assigned. Furthermore the third time information assigned to the third voxel here is larger than the first time information assigned to the first voxel. Furthermore there is no other spatially corresponding voxel with a maximum confidence value, to which time information between the first time information and the third time information is assigned. The interpolation can however be based on other or further voxels as checkpoints, furthermore a non-linear interpolation, by means of polynomials or polynomial trains, is also possible.

Figure 2:
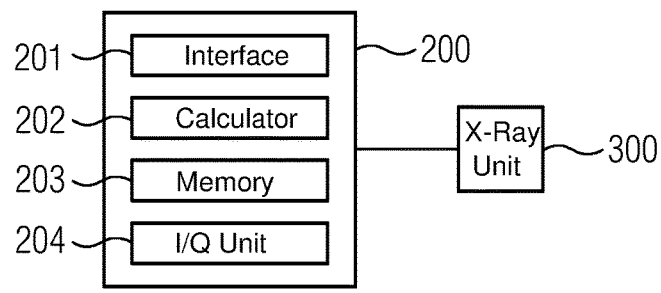
FIG. 2 is a block diagram of a DSA calculation unit.

FIG. 2 shows a DSA calculation unit 200 for calculating a four-dimensional DSA dataset. The DSA calculation unit 200 shown here is designed to carry out an inventive method. The DSA calculation apparatus 200 has an interface 201, a calculation apparatus 202, a memory unit 203 and also an input and output unit 204.

The DSA calculation unit 200 can in particular involve a computer, a microcontroller or an integrated circuit. As an alternative the DSA calculation unit 200 can involve a real or a virtual network of computers (a real network is referred to as a "cluster", a virtual network is referred to as a "cloud"). The interface 201 can involve a hardware or a software interface (for example PCI bus, USB or Firewire). The calculation apparatus 202 can have a hardware element or software elements, for example a microprocessor or what is known as an FPGA (Field Programmable Gate Array). A memory unit 203 can be realized as volatile memory (Random Access Memory, abbreviated to RAM) or as non-volatile mass storage (hard disk, USB stick, SD card, solid state disk). The input and output unit 204 has at least one input unit and/or at least one output unit.

In the exemplary embodiment shown, the DSA calculation unit 200 is connected to an x-ray unit 300. The connection to the x-ray unit 300 can however also be made by a network, for example an intranet or the Internet. The DSA calculation unit 200 can however also be part of the x-ray unit 300. The DSA calculation unit 200 shown here is embodied to carry out the method shown in FIG. 1, in that the interface 201 and the calculation apparatus 202 are embodied to carry out the respective steps of the method.

Figure 3:
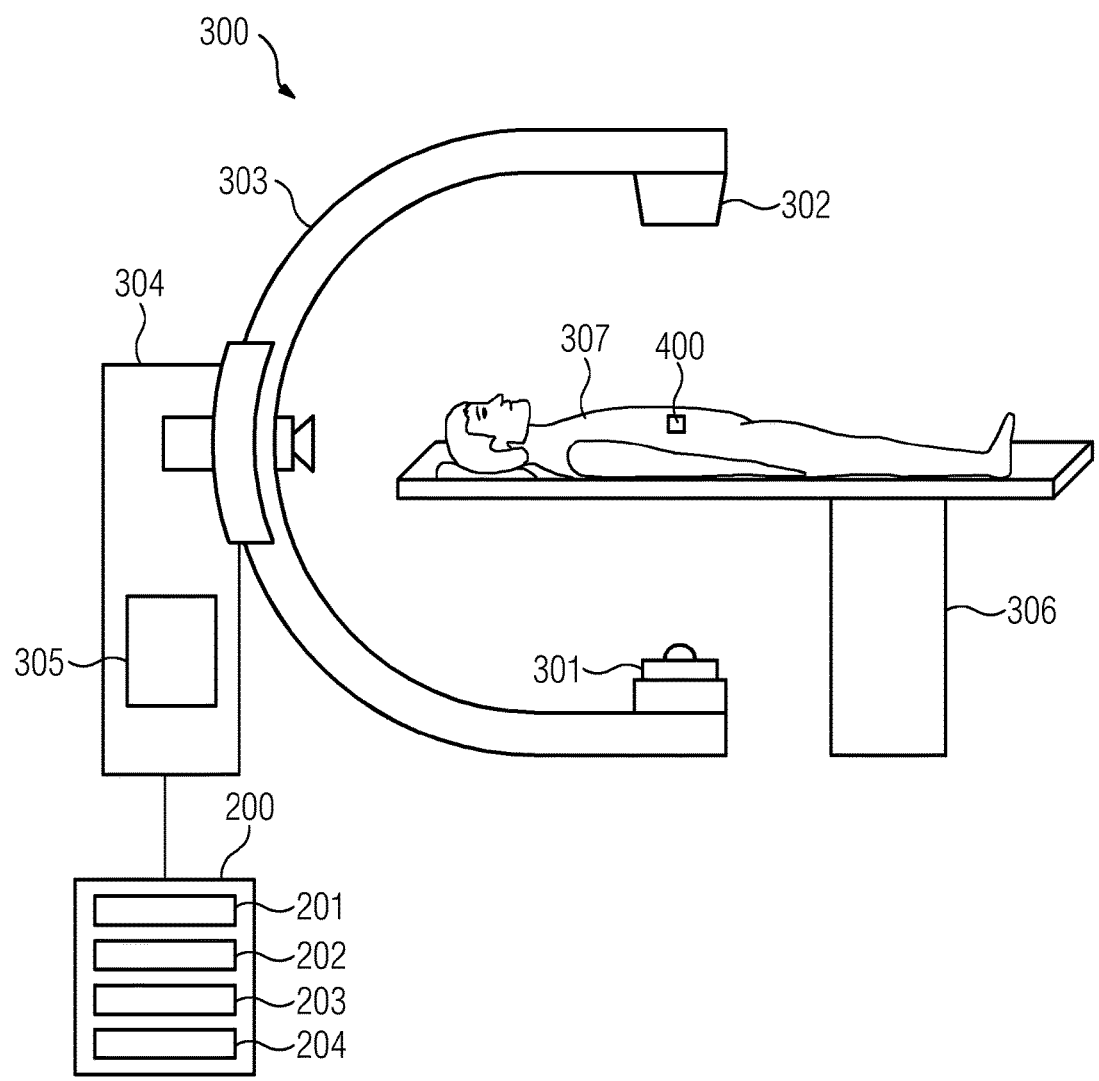
FIG. 3 is an illustration showing an x-ray unit with the DSA calculation unit.

FIG. 3 shows x-ray unit 300 connected to a DSA calculation unit 200. In the exemplary embodiment shown, the x-ray unit 300 involves a C-arm x-ray unit 300. The C-arm x-ray unit 300 has an x-ray source 301 for emitting x-rays. The C-arm x-ray unit 300 further has an x-ray detector 302 for receiving x-rays. The x-ray source 301 and also the x-ray detector 302 are fastened to the two different ends of the C arm 303. The C arm 303 of the C-arm x-ray device 300 is fastened to a pedestal 304. The pedestal 304 has drive elements that are designed to change the position of the C arm 303. In particular the C arm 303 can be rotated around two different axes. The C arm x-ray device further has a control and evaluation unit 305 and also a patient support facility 306, on which a patient 307 can be laid. By means of the control and evaluation unit 305 the position of the C arm 303 can be set and the C arm 303 can be rotated around the examination volume 400. Furthermore two-dimensional x-ray projections of the first examination volume 400 can be recorded and evaluated by means of the control and evaluation unit 305. As an alternative to the exemplary embodiment shown, it is also possible for the DSA calculation unit 200 to be embodied as a part of the control and evaluation unit 305.

Figure 4:
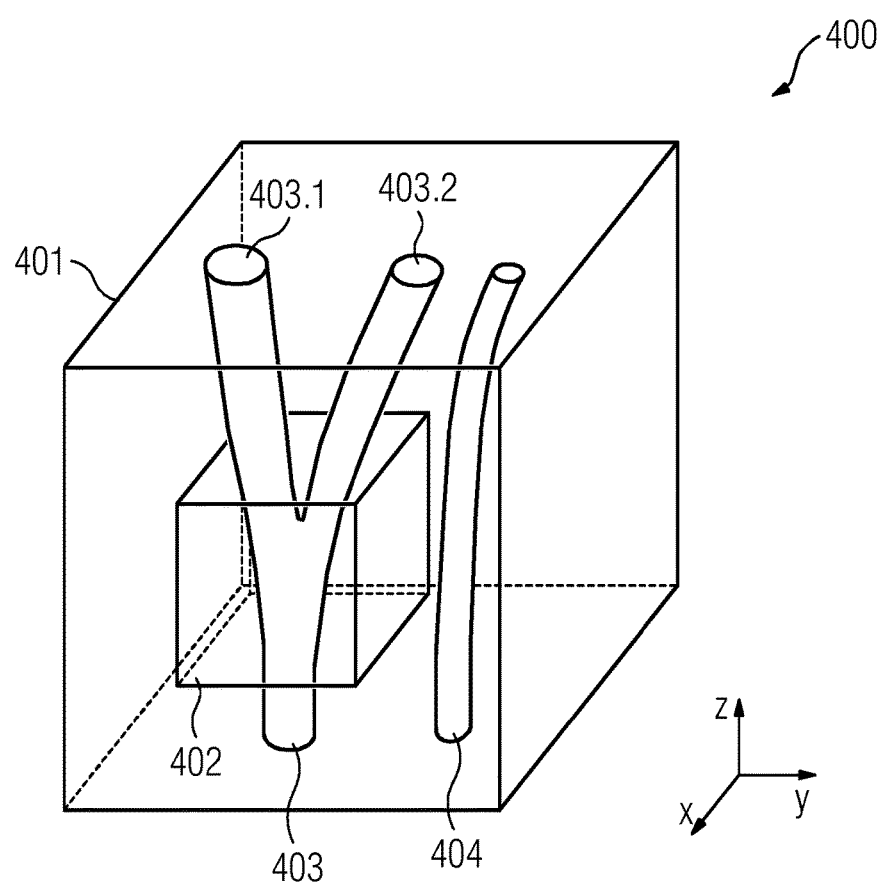
FIG. 4 is a diagrammatic, perspective view of a first and a second vessel in a first examination volume.

FIG. 4 shows an examination volume 400 with a first vessel 403 and a second vessel 404, wherein the examination volume further contains a first reconstruction volume 401 and a second reconstruction volume 402. In the exemplary embodiment shown, the first reconstruction volume 401 is identical to the examination volume 400, but it is also conceivable for the first reconstruction volume 401 to be smaller than the examination volume 400 and to be contained in the examination volume 400. Furthermore the second reconstruction volume 402 is smaller than the first reconstruction volume 401, and the first vessel 403 is split into a first vessel section 403.1 and a second vessel section 403.2. The second vessel 404, in the example shown, runs outside the second reconstruction volume 402, but within the first reconstruction volume 401.

The first reconstruction volume 401 and the second reconstruction volume 402 are embodied here in the shape of cubes, but other geometrical shapes of the first reconstruction volume 401 and of the second reconstruction volume 402 are also conceivable. The edges of the cube-shaped first reconstruction volume 401 and of the cube-shaped second reconstruction volume 402 here are parallel to a first coordinate axis X, to a second coordinate axis Y or to a third coordinate axis Z. The first coordinate axis X, the second coordinate axis Y and the third coordinate axis Z, in the exemplary embodiment shown, form a right-hand Cartesian coordinate system.

Figure 5:
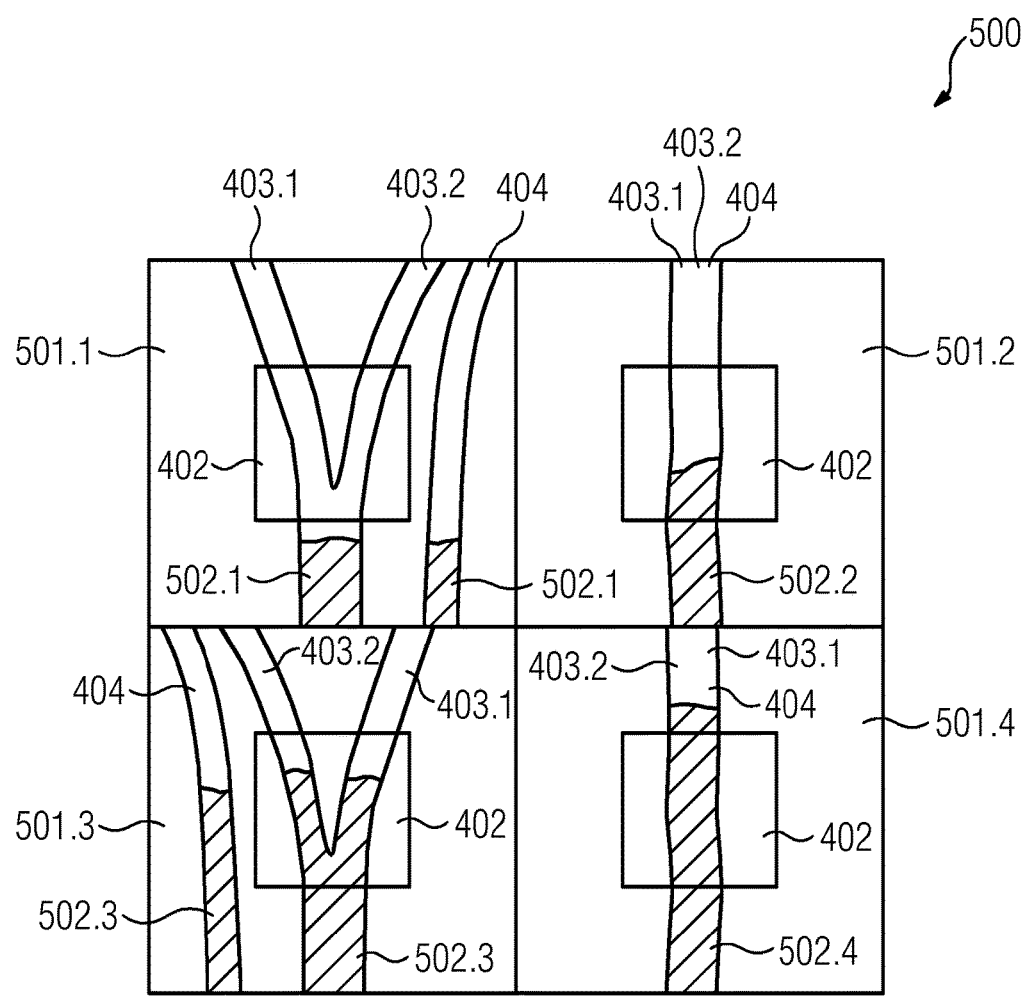
FIG. 5 are x-ray datasets each containing an x-ray projection of the first and of the second vessel.

FIG. 5 shows x-ray datasets 500 each containing one of the four x-ray projections 501.1, 501.2, 501.3 and 501.4, which have been recorded at different recording times. The x-ray projections 501.1, . . . , 501.4 are each projections of the examination volume 400 and thus of the first reconstruction volume 401 from different directions. The projection of the second reconstruction volume 402 is also shown in each case in the x-ray projections 501.1, . . . , 501.4.

The first x-ray projection 501.1 is a projection of the examination volume 400 opposite to the direction of the first coordinate axis X. The second x-ray projection 501.2 is a projection of the examination volume 400 in the direction of the second coordinate axis Y and was recorded at a time after the first x-ray projection 501.1. The third x-ray projection 501.3 is a projection of the examination volume 400 in the direction of the first coordinate axis X and was recorded at a time after the second x-ray projection 501.2. The fourth x-ray projection 501.4 is a projection of the examination volume 400 against the direction of the second coordinate axis Y a and was recorded at a time after the third x-ray projection 501.3.

The x-ray projections 501.1, ..., 501.4 each contain projections of the first vessel 403 and of the second vessel 404. In the second x-ray projection 501.2 and in the fourth x-ray projection 501.4, as a result of the respective direction of projection, the first vessel 403 and the second vessel 404 overlap such that they cannot be displayed individually in the x-ray projection 501.2, 501.4.

Furthermore areas 502.1, ..., 502.4 with high intensity are shown in the x-ray projections 501.1, ..., 501.4. In this exemplary embodiment the areas 502.1, ..., 502.4 correspond to parts of the first vessel 403 and of the second vessel 404 that are filled with a contrast medium. Since the x-ray projections 501.1, ..., 501.4 were recorded at different recording times, the extent of the areas 502.1, ..., 502.4 with high intensity differs in the individual x-ray projections 501.1, ..., 501.4.

If, as is known from the prior art, only one reconstruction volume is used for determining the four-dimensional DSA dataset, then two options are produced in the vessel structure shown. On the one hand the first reconstruction volume 401 can be used as the reconstruction volume, in which the first vessel 403 as well as the second vessel 404 is contained, and in this way the contribution of the second vessel to the x-ray projections 501.1, ..., 501.4 of the x-ray datasets 500 at least by means of an interpolation can be determined. However in this case the four-dimensional DSA dataset has only a coarse spatial resolution. On the other hand the second reconstruction volume 402 can be used as the reconstruction volume, in which only the first vessel 403 is contained, and in this way finer spatial resolution of the four-dimensional DSA dataset can be obtained. However in this case the contribution of the second vessel 404 to the x-ray projections 501.1, ..., 501.4 of the x-ray datasets 500 cannot be determined by calculation. However, in an inventive method, it is possible to obtain both advantages without the respective disadvantages.

The invention claimed is:

1. A method for calculating a four-dimensional digital subtraction angiography (DSA) dataset from x-ray datasets, which comprises the following method steps of:
  receiving the x-ray datasets relating to an examination volume by means of an interface, each of the x-ray datasets containing a two-dimensional x-ray projection of the examination volume in relation to a direction of projection and a recording time of the two-dimensional x-ray projection;
  determining a first three-dimensional DSA dataset of a first reconstruction volume on a basis of the x-ray datasets by means of a calculation unit, wherein the first reconstruction volume is a part of the examination volume or is identical to the examination volume;
  determining a second three-dimensional DSA dataset of a second reconstruction volume on a basis of the x-ray datasets by the calculation unit, wherein the second reconstruction volume is a part of, and smaller than, the first reconstruction volume;
  wherein the first and second three-dimensional DSA datasets have mutually different spatial resolutions;
  segmenting the second three-dimensional DSA dataset by means of the calculation unit;
  normalizing the x-ray datasets on a basis of the first three-dimensional DSA dataset by means of the calculation unit; and
  calculating the four-dimensional DSA dataset by back projection of normalized x-ray datasets onto a segmented second three-dimensional DSA dataset by means of the calculation unit, the four-dimensional DSA dataset having a number of third three-dimensional DSA datasets as well as associated time information.

2. The method according to claim 1, which further comprises calculating each of the third three-dimensional DSA datasets of the four-dimensional DSA dataset by back projection from precisely one of the x-ray datasets being two-dimensional datasets, and wherein the associated time information corresponds to the recording time of the one two-dimensional x-ray dataset.

3. The method according to claim 1, which further comprises the following method steps, each carried out by means of the calculation unit:
  determining a confidence value for at least one first pixel of at least one of a plurality of two dimensional x-ray projections on a basis of the first three-dimensional DSA dataset;
  assigning the confidence value to a first voxel of at least one of the third three-dimensional DSA datasets, wherein a value of the first voxel is based on a value of the first pixel; and
  interpolating the four-dimensional DSA dataset on a basis of the confidence value.

4. The method according to claim 3, wherein the confidence value of the first pixel of the two-dimensional x-ray projection falls monotonously with a number of vessel sections in the first three-dimensional DSA dataset projected onto the first pixel, wherein the vessel sections are projected in a direction of projection of the two-dimensional x-ray projection.

5. The method according to claim 4, wherein an interpolation relates to voxels to which a confidence value smaller than a threshold value is assigned.

6. The method according to claim 1, wherein the first and the second three-dimensional DSA dataset contain homogeneous voxels in each case.

7. The method according to claim 6, wherein an orientation of the homogeneous voxels in the first three-dimensional DSA dataset corresponds to an orientation of the homogeneous voxels in the second three-dimensional DSA dataset.

8. The method according to claim 6, wherein a length of edges of the homogeneous voxels of the second three-dimensional DSA dataset parallel in relation to a first coordinate axis is smaller than a length of edges of the homogeneous voxels of the first three-dimensional DSA dataset parallel in relation to the first coordinate axis.

9. The method according to claim 6, wherein a number of the homogeneous voxels in the first three-dimensional DSA dataset is equal to a number of the homogeneous voxels in the second three-dimensional DSA dataset.

10. The method according to claim 6, wherein edge lengths of the homogeneous voxels of the second three-dimensional DSA dataset are greater than an edge length of pixels of the two-dimensional x-ray datasets.

11. A digital subtraction angiography (DSA) calculation unit for calculating a four-dimensional DSA dataset, comprising:
  a communication interface for receiving x-ray datasets relating to an examination volume, wherein each of the x-ray datasets having has a two-dimensional x-ray projection of an examination volume in relation to a direction of projection and a recording time of the two-dimensional x-ray projection; and
  a processor configured to determine a first three-dimensional DSA dataset of a first reconstruction volume on a basis of the x-ray datasets, wherein a first reconstruction volume is a part of the examination volume or is identical with the examination volume, said processor being further configured for determining a second three-dimensional DSA dataset of a second reconstruction volume on a basis of the x-ray datasets, wherein the first and second three-dimensional DSA datasets have mutually different spatial resolutions and wherein the second reconstruction volume is a part of the first reconstruction volume, said processor being further embodied for segmenting the second three-dimensional DSA dataset, for normalizing of the x-ray datasets on a basis of the first three-dimensional DSA dataset, and calculating the four-dimensional DSA dataset by back projection of normalized x-ray datasets onto a segmented second three-dimensional DSA dataset, wherein the four-dimensional DSA dataset contains a plurality of third three-dimensional DSA datasets as well as associated time information.

12. The DSA calculation unit according to claim 11, wherein said processor is configured for calculating each of the third three-dimensional DSA datasets of the four-dimensional DSA dataset by back projection from precisely one of the x-ray datasets being two-dimensional x-ray datasets, and wherein the associated time information corresponds to a recording time of a two-dimensional x-ray dataset.

13. An x-ray unit for recording x-ray datasets, comprising: a digital subtraction angiography calculation unit according to claim 10.

14. A non-transitory computer-readable storage medium comprising executable instructions to be read and executed by a digital subtraction angiography (DSA) calculation unit which comprises the steps of:

receiving x-ray datasets relating to an examination volume by means of a communication interface, each of the x-ray datasets containing a two-dimensional x-ray projection of the examination volume in relation to a direction of projection and a recording time of the two-dimensional x-ray projection;

determining a first three-dimensional DSA dataset of a first reconstruction volume on a basis of the x-ray datasets by means of a processor, wherein the first reconstruction volume is a part of the examination volume or is identical to the examination volume;

determining a second three-dimensional DSA dataset of a second reconstruction volume on a basis of the x-ray datasets by the calculation apparatus processor, wherein the second reconstruction volume is a part of the first reconstruction volume;

wherein the first and second three-dimensional DSA datasets have mutually different spatial resolutions;

segmenting the second three-dimensional DSA dataset by means of the processor;

normalizing the x-ray datasets on a basis of the first three-dimensional DSA dataset by means of the processor; and calculating a four-dimensional DSA dataset by back projection of normalized x-ray datasets onto a segmented second three-dimensional DSA dataset by means of the processor, the four-dimensional DSA dataset having a plurality of third three-dimensional DSA datasets as well as associated time information.

\* \* \* \* \*